(12) United States Patent
Yde

(10) Patent No.: US 9,308,271 B2
(45) Date of Patent: Apr. 12, 2016

(54) COMPOSITIONS

(75) Inventor: Birgitte Yde, Farum (DK)

(73) Assignee: CHR. HANSEN A/S, Hoersholm (DK)

(*) Notice: Subject to any disclaimer, the term of this patent is extended or adjusted under 35 U.S.C. 154(b) by 46 days.

(21) Appl. No.: 14/129,851

(22) PCT Filed: Jun. 30, 2012

(86) PCT No.: PCT/EP2012/062787
§ 371 (c)(1),
(2), (4) Date: Mar. 27, 2014

(87) PCT Pub. No.: WO2013/001089
PCT Pub. Date: Jan. 3, 2013

(65) Prior Publication Data
US 2014/0255366 A1    Sep. 11, 2014

(30) Foreign Application Priority Data

Jun. 30, 2011 (EP) ................................. 11172132
Jul. 5, 2011 (EP) ................................. 11172697
Dec. 5, 2011 (EP) ................................. 11191955

(51) Int. Cl.
| | | |
|---|---|---|
| C12N 1/20 | (2006.01) |
| A01N 63/00 | (2006.01) |
| A61K 47/36 | (2006.01) |
| A23L 1/03 | (2006.01) |
| C12N 1/04 | (2006.01) |
| A23L 1/30 | (2006.01) |
| A23L 1/305 | (2006.01) |
| A23L 1/308 | (2006.01) |
| A23L 1/29 | (2006.01) |
| A61K 35/747 | (2015.01) |
| A61K 47/22 | (2006.01) |

(52) U.S. Cl.
CPC ............ *A61K 47/36* (2013.01); *A23L 1/0345* (2013.01); *A23L 1/296* (2013.01); *A23L 1/3014* (2013.01); *A23L 1/3053* (2013.01); *A23L 1/3056* (2013.01); *A23L 1/3081* (2013.01); *A61K 35/747* (2013.01); *A61K 47/22* (2013.01); *C12N 1/04* (2013.01); *C12N 1/20* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 8,377,430 B2* | 2/2013 | Donnet-Hughes et al. | 424/93.1 |
| 2004/0202765 A1* | 10/2004 | McMahon et al. | 426/580 |
| 2005/0100559 A1 | 5/2005 | Myatt et al. | |
| 2007/0031475 A1* | 2/2007 | Kuslys et al. | 424/439 |
| 2010/0316619 A1* | 12/2010 | Wittke | 424/93.45 |
| 2011/0070334 A1 | 3/2011 | Rangavajla | |
| 2012/0039852 A1* | 2/2012 | Darimont-Nicolau et al. | 424/93.3 |

FOREIGN PATENT DOCUMENTS

| | | |
|---|---|---|
| EP | 0 259 739 | 3/1988 |
| EP | 1 441 027 | 7/2004 |
| WO | WO-2010/049539 | 5/2010 |
| WO | WO-2010/138522 A2 | 12/2010 |

OTHER PUBLICATIONS

Carcoba et al. "Influence of cryoprotectants on the viability and acidifying activity of frozen and freeze dried cells of the novel starter strain *Lactococcus lactis* ssp. *lactis* CECT 5180." European Food Research and Technology, vol. 211, Jan. 2000, pp. 433-437.

Carvalho et al. "Survival of freeze-dried *Lactobacillus plantarum* and *Lactobacillus rhamnosus* during storage in the presence of protectants." Biotechnology letters, vol. 24, Oct. 2002, pp. 1587-1591.

Kurtmann et al. "Storage stability of freeze dried *lactobacillus acidophilus* (La-5) in relation to water activity and presence of oxygen and ascorbate." Cryobiology, vol. 58, Apr. 2009, pp. 175-180.

Oldenhof et al. "Effect of sucrose and maltodextrin on the physical properties and survival of air-dried *Lactobacillus bulgaricus*: an in situ fourier transform infrared spectroscopy study." vol. 21, Jan. 2005, pp. 885-892.

Siaterlis et al. "Effect of culture medium and cryoprotectants on the growth and survival of probiotic *lactobacilli* during freeze drying." Letters in applied microbiology, vol. 48, Mar. 2009, pp. 295-301.

PCT/EP2012/062787, International Search Report mailed Sep. 3, 2012.

\* cited by examiner

*Primary Examiner* — Chris R Tate
*Assistant Examiner* — Douglas F White
(74) *Attorney, Agent, or Firm* — Foley & Lardner LLP

(57) ABSTRACT

The invention relates to a dry compositions for lactic acid bacteria and in particular to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition): from 6 to 9 g of trehalose, from 0.1 to 1 g of inulin and from 0.5 to 3 g of hydrolyzed casein, and by that it does not comprise a salt of alginic acid. The composition has an improved storage stability of the cell of interest. Comparison experiments have been made between compositions with and without alginate and it has been found that there is substantially no difference between compositions with or without alginate with regard to stability. Further, the invention relates to a method for preparing a dry lactic acid bacteria composition.

14 Claims, 4 Drawing Sheets

COMPOSITIONS

RELATED APPLICATIONS

This application is a national phase of international application PCT/EP/2012/062787, flied Jun. 30, 2012, which was published on Jan. 3, 2013, as WO 2013/001089, which claims the benefit of European applications No. 11172132.0, flied Jun. 30, 2011, No. 11172697.2, filed Jul. 5, 2011, and No. 11191955.1, filed Jun. 30, 2011. The respective contents of these applications are incorporated here by reference in their entirety.

FIELD OF THE INVENTION

The present invention relates to the field of dry compositions for lactic acid bacteria, a method for preparing dry lactic acid bacteria compositions and compositions which may be prepared by said method.

BACKGROUND OF THE INVENTION

Cells such as e.g. microorganisms are involved in numerous industrially relevant processes. for instance bacterial cultures, in particular cultures of bacteria that are generally classified as lactic acid bacteria (LAB) are essential in the marking of all fermented milk products, cheese and butter. Cultures of such bacteria may be referred to as started cultures and they impart specific features to various dairy products by performing a number of functions.

Many lactic acid bacteria are known to have probiotic properties (i.e. they have a beneficial health effect on humans when ingested). In most cases, it is imperative that the microorganisms remain viable after prolonged storage, in order for these to impart their beneficial effect on ingestion. Attempts have been made, in which freeze dried bacteria are mixed with additives that act as moist barriers, or as protectants needed for freezing the cells (so called cryo-protectants). Various types of additives have been added to the microorganisms in attempts to make them more stable.

For some uses—one may say that one preferably shall have a very storage stable lactic acid bacteria composition/formulation.

For instance—if the LAB composition is mixed with milk powder to make a suitable infant powder, one generally needs a very storage stable LAB composition—essentially due to than an infant powder product as such is normally very storage stable and may be given to infants quite a ling time after is actual fabrication date. Accordingly, if the infant powder is given to infants e.g. 30 weeks (or later) after its actual fabrication date—it is evident that the LAB composition incorporated into the infant powder should be quite storage stable in order to maintain viability of the LAB cells.

WO2010/138522A2 (Advanced Bionutrition Corporation) describes a LAB cell culture composition that is explained to be useful to be incorporated into an infant powder product.

A preferred composition comprises alginate, inulin, trehalose and hydrolyzed protein (see table 1, paragraph [0094]).

One may say that the LAB compositions of table 1 of WO2010/138522A2 comprise a relatively high amount of what may be termed protective agents—i.e. agent that could help to improve the storage stability of lactic acid bacteria cells.

For instance—one may say that the LAB compositions of table 1 of WO2010/138522A2 comprise a relatively high amount of trehalose.

Paragraph [0097] of WO2010/138522A2 reads:

"*Lactobacillus Acidophilus* (100 g frozen concentrate from a lab fermentation harvest) was thawed at 37 C. Protein hydrolysate premix (100 g, Table 1) . . . "

As known to the skilled person, a LAB cell concentrate, as described in this paragraph [0097], may often comprise around 10% dry matter of cells. Under this assumption—one may say that the dried LAB composition described in this paragraph [0097] is a LAB composition that comprises around 10 times more protective agents than LAB cells as such—according to the art, this may be said to be a LAB composition with a relatively high amount of protective agents.

A problem with such LAB compositions with a relatively high amount of protective agents may be that they often can be quite difficult to properly dry as such—e.g. without significantly inactivation of the relevant LAB cells.

WO2010/138522A2 describes processes for drying e.g. the in paragraph [0097] described LAB composition, which as discussed above may say said to be a LAB composition with a relatively high amount of protective agents.

Paragraph [0081] of WO2010/138522A2 reads (emphasis added):

"Typical processes for preservation of bioactive microorganisms such as, live or attenuated organisms include a combination of freezing and vacuum conditions that can result in membrane damage and denaturation of cell constituents. The prior art teaches the use of higher vacuum pressures (e.g., less than 100 Torr), addition of specific cryoprotective agents, concentrating steps to obtain thick solutions (syrup), and/or higher initial temperatures to prevent freezing."

This paragraph [0087] of WO2010/138522A2 may be said to provide an overall summary of what the prior art generally teaches with respect to suitable herein relevant drying processes.

It may herein be said to be relevant to note that the drying method directly and unambiguously described in WO2010/138522A2 is e.g. not involving a freezing step to form solid frozen particles/pellets.

WO2010/138522A2 (Advanced Bionutrition Corporation) describes a cell culture composition comprising alginate, inulin, trehalose and hydrolyzed protein (see table 1, paragraph [0094]).

However, there is still a need for improved compositions which are able to withstand elevated humidity/high water activity.

SUMMARY OF THE INVENTION

The problem to be solved by the present invention relates to the provision of a new method for preparing a dry powder composition comprising lactic acid bacteria (LAB) cells and what may be said to be a relatively high amount of protective agents and the provision of compositions which are storage stable for prolonged time under humid conditions.

In a preferred embodiment, the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 6 to 9 g of trehalose,
from 0.1 to 1 g of inulin and
from 0.5 to 3 g of hydrolyzed casein, and by
that it does not comprise a salt of alginic acid.

Reference is made to the working examples herein, wherein it is demonstrated that the storage stability of the LAB cell *Lactobacillus rhamnosus* LGG®, which is commercially composition as described herein. The present inventors also made experiments with the LAB cell *L. casei* 431® (*Lactobacillus paracasei* subsp. *paracasei*)—and good storage stability was also demonstrated for dry compositions as described herein.

As illustrated in working examples herein, the new compositions as described herein result in an improved storage stability of the cells. In particular, the compositions are more stable at elevated humidity/high water activity. The present invention provides compositions comprising LAB in infant powder with a water activity of 0.3 wherein the log loss of active cells is <2.5 when stored at 30% RH at 35° C. and tested after 13 weeks. Preferably, the compositions log loss of active cells is <2.5 after 17 weeks.

As demonstrated in the examples, substantially no difference is seen between compositions with or without sodium alginate with regard to stability. However, for compositions with sodium alginate which have been subjected to heat treatment, the heat treatment has a negative impact on stability in contrast to the compositions without sodium alginate.

Accordingly, one aspect of the invention relates to a dry composition comprising from $10^9$ to $10^{13}$ cfu/g of the composition of lactic acid bacteria cells, wherein the composition is characterized by that it also comprises a relatively high amount of protective agents as described in further detail in the following. Preferably, the composition does not comprise a salt of alginic acid such as sodium alginate for reasons explained in further detail later.

As discussed herein—a dry composition as described herein can be used in e.g. infant powder with high water activity (a'=0.3) or in other high a" applications like cereals, muesli bars or chocolate.

The solution is based on that the present inventors have worked intensively with numerous different parameters for drying such compositions and identified that by using the drying method as described herein one is able to properly dry such compositions in an efficient way that can be applied on industrial scale with relatively large amounts of the LAB composition—i.e. it can be made at relatively low costs and the drying can be performed within a relatively short period (e.g. within from 15 to 30 hours).

As discussed above—the drying method directly and unambiguously described in WO2010/138522A2 is e.g. not involving a freezing step to form solid frozen particles/pellets. The drying method as described herein also comprises other method steps that are different from what is directly and unambiguously described in WO2010/138522A2.

For instance—in primary drying step (e) of the method of the first aspect of the invention is used a vacuum pressure of from 0.7 to 2 millibar (mbar) (corresponding to 525 mTORR to 1500 mTORR). As discussed herein—use of this vacuum pressure range of from 0.7 to 2 mbar may be seen as a herein essential element of the method of the invention. As discussed herein—it is only working within this vacuum pressure range of from 0.7 to 2 mbar in step (e) that one gets a herein satisfactory method for drying a herein relevant LAB.

Use of this range of from 0.7 to 2 mbar as done in step (e) herein is not described or suggested in WO2010/138522A2 or any other herein relevant to the inventors known prior art.

In short, it is submitted that the drying method of the present invention represents a significant improvement over the drying methods directly and unambiguously described in e.g. WO2010/138522A2.

Accordingly, a first aspect of the invention relates to a method for preparing a dry powder composition comprising:
  (i): from $10^8$ to $10^{14}$ cfu/g of the composition of lactic acid bacteria (LAB) cells; and
  (ii) an amount of protective agent(s) of from 2 g to 40 g—wherein the amount of protective agent(s) is given relative to 1 g of lactic acid bacteria cells in the dry composition, wherein the method for preparing a dry powder composition comprises following steps:
  (a): fermenting the LAB cell and harvesting the cells to get a LAB cell concentrate comprising the LAB cells and water—wherein the concentrate comprises from $10^8$ to $10^{11}$ cfu/g dry matter of the concentrate of lactic acid bacteria (LAB) cells;
  (b): mixing a suitable amount of protective agent(s) with the LAB cell concentrate to form a slurry—wherein the slurry comprises an amount of protective agent(s) of from 2 g to 40 g—wherein the amount of protective agent(s) is given relative to 1 g of lactic acid bacteria cells in the slurry and both the amount of protective agent(s) and lactic acid bacteria cells are measured as dry matter in a slurry;
  (c): freezing the slurry to form solid frozen particles/pellets;
  (d): loading a tray with from 2 kg/m² to 50 kg/m² of the frozen particles/pellets to get the herein relevant material on the tray;
  (e): primary drying the material on the tray under a vacuum pressure of from 0.7 to 2 millibar (mbar), at a temperature wherein the temperature of the material does not get so high that more than 75% of the LAB cells are inactivated and for a period of time until at least 90% of the water of the slurry of step (b) has been removed; and
  (f): secondary drying the material of step (e) under a vacuum pressure of from 0.01 to 0.6 millibar(mbar), at a temperature wherein the temperature of the material does not get so high that more than 75% of the LAB cells are inactivated and for a period of time sufficient to reduce the water activity ($a_w$) to less than 0.30 and thereby obtaining the dry powder composition comprising:
  (i): from $10^8$ to $10^{11}$ cfu/g of the composition of lactic acid bacteria (LAB) cells; and
  (ii) an amount of protective agent(s) of from 2 g to 40 g—wherein the amount of protective agent(s) is given relative to 1 g of lactic acid bacteria cells in the dry composition.

The term "protective agent(s)" shall herein be understood as any agent that could help to improve the storage stability of lactic acid bacteria cells of interest. In relation to a dry powder composition and the method of drying such a dry powder composition as described herein—the term "protective agent(s)" may also be seen as any agents present in the dry powder composition as such, which is not the lactic acid bacteria (LAB) cells as such.

As understood by the skilled person in the present context—the term "wherein the amount of protective agent(s) is given relative to 1 g of lactic acid bacteria cells in the dry composition"—means that if the dry powder composition of the first aspect e.g. comprises 2 g of lactic acid bacteria cells then shall the dry powder composition also comprise from 4 g to 80 g of protective agent(s)—since the method of the first aspect says that there shall be from 2 g to 40 g of protective agent(s) per 1 g of lactic acid bacteria cells.

Similarly, as understood by the skilled person in the present context—the term "all amounts of protective agents below are given relative to 1 g of active lactic acid bacteria cells in the composition" means that if the composition e.g. comprises 2 g of lactic acid bacteria cells then shall the composition e.g. also comprise from 4 to 8 g of sucrose.

Since the composition is a dry powder composition—is it evident to the skilled person that the amounts given for the individual components (e.g. lactic acid bacteria cells and protective agents) of the composition are measured as dry matter.

A composition as described herein may be included in a suitable package—e.g. a bottle, box, vial, capsule etc. As would be understood by the skilled person in the present context—when there herein is referred to the weight of the composition (e.g. termed "g of the composition") then there is referred to the weight of the composition as such—i.e. not including the possible weight of a suitable package.

Embodiments of the present invention are described below, by way of examples only. Below are described further herein relevant dry compositions—wherein one may say that each of them is characterized by specific preferred amounts of protective agents.

One aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 2 to 5 g of sucrose, from 1 to 3 g of maltodextrin and from 0.75 to 2 g of Na-ascorbate.

A second aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 5 to 9 g of sucrose, from 1 to 3 g of maltodextrin and from 0.75 to 2 g of Na-ascorbate.

A third aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 3 to 6 g of sucrose, from 4 to 8 g of trehalose and from 0.0 (preferably 0.1) to 0.5 g of Na-ascorbate.

A fourth aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 0.5 to 3.5 g of maltodextrin, from 0.0 (preferably 0.1) to 0.5 g of Na-ascorbate, from 6 to 9 g of trehalose and from 0.1 to 0.5 g of modified starch.

The term "modified starch" is well known to the skilled person and the skilled person knows if a specific agent of interest is modified starch or not. As known to the skilled person—modified starch, also called starch derivatives, are prepared by physically, enzymatically, or chemically treating native starch. A herein suitable commercially available modified starch is the commercial available Remy HC-P modified starch product.

A fifth aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 6 to 9 g of trehalose, from 0.1 to 1 g of inulin and from 0.5 to 3 g of hydrolyzed casein.

A sixth aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 0.5 to 3.5 g of maltodextrin, from 0.0 (preferably 0.1) to 0.5 g of Na-ascorbate and from 2 to 5 g of trehalose.

A seventh aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 2 to 5 g of sucrose, from 1.5 to 3.5 g of maltodextrin and from 0.0 (preferably 0.1) to 0.5 g of Na-ascorbate.

An eighth aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 4.5 to 7.5 g of sucrose, from 2.5 to 5.5 g of maltodextrin and from 0.0 (preferably 0.1) to 0.5 g of Na-ascorbate.

A ninth aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 2.5 to 5.5 g of maltodextrin and from 0.0 (preferably 0.1) to 0.5 g of Na-ascorbate and from 4.5 to 7.5 g of trehalose.

A tenth aspect of the invention relates to a dry composition comprising from $10^9$ to $10^{13}$ cfu/g of the composition of lactic acid bacteria cells, wherein the composition is characterized by that it also comprises following amounts of protective nr.ritc (all amounts of protective agents below are given relative to 1 g of lactic acid bacteria cells in the composition):

(i): from 1.5 to 4.5 g of maltodextrin and from 0.0 (preferably 0.1) to 0.5 g of Na-ascorbate and from 3 to 6 g of trehalose.

An eleventh aspect of the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 0.5 to 3 g of maltodextrin and from 0.0 (preferably 0.1) to 0.5 g of Na-ascorbate and from 1 to 4 g of trehalose.

Experimental results have demonstrated that all the above described dry compositions have very good storage stability.

Generally the specific preferred industrial use of a lactic acid bacteria (LAB) cell containing composition as described herein would normally depend on the specific characteristics of the cell in question.

The composition may be given to a human, an animal or a fish for health-promoting purposes. This is generally most relevant if the cell has probiotic properties and is particularly relevant when the cell is a probiotic LAB cell.

Accordingly, a further aspect of the invention, relates to a method for giving lactic acid bacteria (LAB) cells to a human, an animal or a fish, comprising administrating at least one dry composition of any of the separate dry composition aspects as described herein.

DETAILED DESCRIPTION OF THE INVENTION

Dry Powder Composition

Figure 1:
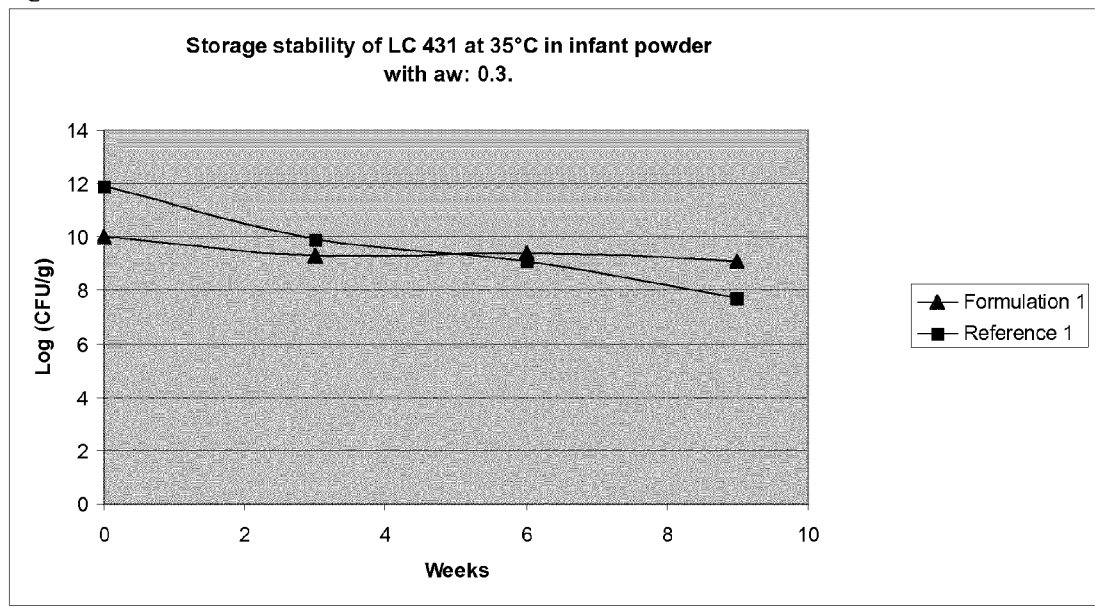
FIG. 1 shows storage stability for *L. casei* 431(1) compositions in infant powder with $a_w$: 0.3 and at a storage temperature of 35° C.

The skilled person understands what a dry composition is in the present context. To describe this quantitatively—the water activity ($a_w$) of dry powder composition as described herein is less than 0.30. More preferably—the water activity ($a_w$) of dry powder composition as described herein is less than 0.25, even more preferably less than 0.20 and most preferably the water activity ($a_w$) of dry powder composition as described herein is less than 0.15. The skilled person knows how to determine the water activity ($a_w$) of dry composition as described herein.

The skilled person knows how to manufacture a dry composition as described herein. The manufacture of the dry composition as described herein involves e.g. mixing a cell culture with a protective agent. The second step involves drying said mixture. The drying may be done by freeze drying, spray drying, modified spray drying and/or vacuum drying. Other means for drying may be possible.

In case of freeze- or vacuum-drying, the mixture is preferably formed into pellets by methods which are known in the art. One method may be to let drops of the mixture fall into liquid nitrogen. Another method for forming pellets may be by extrusion. Said pellets may subsequently be dried, using the above drying methods. Preferably, the composition is dried using the method for preparing a dry powder composition described herein.

The dry composition may be in a powder form.

The weight of the dry composition (e.g. termed "g of the composition") will generally depend on different factors such as the use of the composition (e.g. to make an infant powder product as discussed below).

The weight of the dry composition as described herein may e.g. be from 1 g to 1000 kg.

For instance—if the dry composition is to be used as an infant product—then is the dry composition generally mixed with milk powder and other supplements to get an infant powder product comprising lactic acid bacteria cells.

As known to the skilled person—production of infant powder products may be done on a quite large scale—e.g. by mixing from 1 to 10 kg of a dry composition as described herein with a suitable amount of milk powder and other supplements.

Accordingly, it may be preferred that the weight of the dry composition as described herein is from 50 g to 10000 kg, such as e.g. from 100 g to 1000 kg or from 1 kg to 5000 kg or from 100 kg to 1000 kg.

As evident to the skilled person in the present context—in order to obtain, in step (f) of the method of first aspect, a dry powder composition with a weight of e.g. 100 kg—one needs to use corresponding relatively high amounts of LAB cell concentrate in step (b) of first aspect and protective agent(s) in step (c) of the first aspect.

The dry powder composition of the invention may be encapsulated, e.g. in a gelatine capsule, or formulated into e.g. tablets, or sachets. This aspect is particularly relevant if the composition is to be used in a dietary supplement.

Lactic Acid Bacteria Cells

It may be preferred that the dry powder composition as described herein comprises from $10^1$ to $10^{13}$ cfu/g of the composition of lactic acid bacteria (LAB) cells.

The lactic acid bacteria (LAB) cell may in principle be any suitable LAB cell of interest.

Preferably, the LAB cell is a probiotic cell.

The expression "probiotic cell" designates a class of cells (e.g. micro-organisms) which is defined as a microbial food or feed supplement which beneficially affects the host human or animal by improving its gastrointestinal microbial balance. The known beneficial effects include improvement of the colonization resistance against the harmful micro-flora due to oxygen consumption and acid production of the probiotic organisms. An example of the efficacy of probiotically active organisms to prevent overgrowth of potential pathogens and thus diarrhea, is shown in a study where the administration of capsules containing viable probiotically active organisms to tourists traveling in Egypt resulted in a protection rate of 39.4% against traveler's diarrhea (Black et al. 1989). A review of probiotics and their effects in man and animals can be found in Fuller, 1989 and 1994.

In the present context, the expression "lactic acid bacteria" designates a group of Gram positive, catalase negative, non-motile, microaerophilic or anaerobic bacteria which ferment sugar (including lactose) with the production of acids including lactic acid as the predominantly produced acid, acetic acid, formic acid and propionic acid. Below are described herein preferred LAB.

The industrially most useful lactic acid bacteria are found among *Lactococcus* species, *Streptococcus* species, *Enterococcus* species, *Lactobacillus* species, *Leuconostoc* species, *Bifidobacterium* species, *Propioni* and *Pediococcus* species. Accordingly, in a preferred embodiment the lactic acid bacteria are selected from the group consisting of these lactic acid bacteria.

In a preferred embodiment the lactic acid bacteria are lactic acid bacteria selected from the group consisting of *Lactobacillus rhamnosus, Lactococcus lactis* subsp. *lactis, Lactococcus lactis* subsp. *cremoris, Leuconostoc lactis, Leuconostoc mesenteroides* subsp. *cremoris, Pediococcus pentosaceus, Lactococcus lactis* subsp. *lactis* biovar. *diacetylactis, Lactobacillus casei* subsp, *casei, Streptococcus thermophilus, Enterococcus*, such as Entr-rnrnrriK *faecum, Bifidobacte-* rium animalis, Bifidobacterium lactis, Bifidobacterium longum, Lactobacillus lactis, Lactobacillus helveticus, Lactobacillus fermentum, Lactobacillus salivarius, Lactobacillus delbrueckii subsp. bulgaricus and Lactobacillus acidophilus. Within this group, the most preferred lactic acid bacterium is Lactobacillus rhamnosus.

The composition may comprise one or more strain(s) of a lactic acid bacterium which may be selected from the group comprising: BB-12® (Bifidobacterium animalis subsp lactis BB40 12®), DSM 15954; ATCC 29682, ATCC 27536, DSM 13692, and DSM 10140, LA-5® (Lactobacillus acidophilus LA-5®), DSM 13241, LGG®) (Lactobacillus rhamnosus LGG®), ATCC 53103, GR-1® (Lactobacillus rhamnosus GR-1®), ATCC 55826, RC-14® (Lactobacillus reuteri RC-14g), ATCC 55845, L. casei 431® (Lactobacillus paracasei subsp. paracasei L. casei 431®), ATCC 55544, F19® (Lactobacillus paracasei F19®), LMG-17806, TH-4® (Streptococcus thermophilus TH-4®)), DSM 15957, PCC®) (Lactobacillus fermentum PC00), NM02/31074, LP-33® (Lactobacillus paracasei subsp. paracasel LP-33®), CCTCC M204012.

The LAB culture may be a "mixed lactic acid bacteria (LAB) culture" or a "pure lactic acid bacteria (LAB) culture". The term "mixed lactic acid bacteria (LAB) culture", or "LAB" culture, denotes a mixed culture that comprises two or more different LAB species. The term a "pure lactic acid bacteria (LAB) culture" denotes a pure culture that comprises only a single LAB species. Accordingly, in a preferred embodiment the LAB culture is a LAB culture selected from the group consisting of these cultures.

The LAB culture may be washed, or non-washed, before mixing with the protective agents. If the composition comprises a salt of alginic acid such as sodium alginate, it is often necessary to wash the cells with demineralized water before the addition of the protective agents to avoid the formation of calcium alginate.

Protective Agent(s)

The term "protective agent(s)" shall herein be understood as any agent that could help to improve the storage stability of lactic acid bacteria cells of interest. In relation to a dry powder composition and the method of drying such a dry powder composition as described herein—the term "protective agent(s)" may also be seen as any agents present in the dry powder composition as such, which is not the lactic acid bacteria (LAB) cells as such.

It may be preferred that the amount of protective agent(s) of point (ii) of the first aspect is 30 an amount of protective agent(s) of from 4 g to 20 g, such as from 5 g to 15 g or from 6 g to 12 g.

In a preferred embodiment—at least 30% (more preferably at least 50%, even more preferably at least 70% (such as e.g. at least 80% or at least 90%) of the protective 35 agent(s) of point (ii) of the first aspect are carbohydrates.

Preferably the carbohydrates are saccharides and preferred saccharides are e.g. sucrose, maltodextrin, trehalose and/or inulin.

In working examples herein is described drying of a LAB composition, wherein more than 80% of the protective agent(s) are saccharides, since the composition comprises 75.3 g trehalose+5.0 g inulin per 100 g of all the protective agents present in the composition.

Further, below is discussed other herein preferred dry powder LAB compositions, wherein more than 70% of the protective agent(s) are saccharides. Without being limited of theory—it is believed that all these herein described "more than 70% of the protective agent(s) are saccharides" LAB compositions have a very good storage stability—said in other words, by using a (as described herein) relatively high amount of carbohydrates (such as e.g. saccharides) as protective agents one may obtain a dry powder LAB composition with a commercially relevant very good storage stability (e.g. for use as component in an infant powder).

As used herein, by the term "infant" is meant a human from about birth to 12 months or age. In the present context, the term "infant formula" refers to a composition in liquid or powdered form that satisfies the nutrient requirements of an infant by being a substitute for human milk. These formulations are regulated by EU and US regulations which define macronutrient, vitamin, mineral and other ingredient levels in an effort to simulate the nutritional and other properties of human breast milk. Evidently, the formula should not contain any potentially allergizing substances. Thus, when hydrolyzed casein is used, it should preferably be hydrolyzed so that over 90% of the peptides have a molecular weight of less than 1,000 Daltons, with over 97% having a molecular weight of less than 2,000 Daltons.

As used herein, "children" are defined as humans over the age of about 12 months to about 12 years old. The infant powder compositions of the present invention may be used for infant formula, follow-on formula, growing up milk and special formula as well as for infant and children's nutritional product for improving their gut microflora while simultaneously providing nutrition to the infant or child.

A herein suitable protective agent is a protective agent selected from the group consisting of: Na-ascorbate, modified starch, hydrolyzed casein and alginate (e.g. sodium alginate).

Alginic acid, also called algin or alginate, is an anionic polysaccharide distributed widely in the cell walls of brown algae. Alginate is present in the cell walls of brown algae as the calcium, magnesium and sodium salts of alginic acid. Alginic acid form water-soluble salts with monovalent cations but is precipitated upon acidification.

Alginates of many bivalent cations, particularly of Ca2+, Sr2+ and Ba2+, are insoluble in water and can be prepared when sodium ions of NaAlg are replaced by di- and trivalent cations. This property is used in the isolation of alginic acid from algae. The goal of the extraction process is to obtain dry, powdered, sodium alginate. The calcium and magnesium salts do not dissolve in water; the sodium salt does.

Due to their physical and chemical properties the monovalent salts of alginic acid such as h hydrogen alginate (1IA1g), potassium alginate (KaAlg) and sodium alginate (NaAlg), have widely been used in food processing, medical and pharmaceutical industries. In contrast, calcium alginate is a water-insoluble, gelatinous, cream coloured substance that can be created through the addition of aqueous calcium chloride to aqueous sodium alginate.

When the composition is to be used in an infant powder, it is preferred that it does not contain modified starch or polysaccharides such as sodium alginate as sodium alginate which is a product extracted from algae is not approved for use in infant powder for infants younger than 1 year (infant formula). For this reason comparison of a number of compositions without alginate have been prepared and it has been found as demonstrated in the examples that these compositions exhibit a good stability. Further comparison experiments have been made between compositions with and without alginate and it has been found that there is substantially no difference between compositions with or without alginate with regard to stability.

Important disadvantages by using alginate which is a product extracted from algae as described above is that there is a large batch-to-batch variation with regard to viscosity and that the product may contain bacteria meaning that some treatment, e.g. heat treatment has to be applied in order to inactivate the bacteria. The heat treatment can be any given combination of temperature and holding time which achieves a log 6 reduction or more (F0-value equal to or more than 6), i.e. it can be a batch heat treatment in a pressurized tank with a heating mantle, the use of sterile steam injection/condensation directly into the protective agent solution (both fairly long duration at 110-121 C) or continuously through an UHT-treatment unit (short duration at high temperature, i.e. 30 sec at 132 C).

This treatment leads to depolymerization of the alginate and heat treatment generally has a negative impact on stability for compositions with sodium alginate as demonstrated in Example 9.

Thus, in contrast to the conventional teaching in the art to include salts of alginic acid such as sodium alginate in compositions for stabilizing and protecting live bacteria during harsh conditions, it is advantageous for the above reasons to provide compositions that do not comprise salts of alginic acid such as sodium alginate. Accordingly the compositions of the present invention preferably do not comprise a salt of alginic acid such as sodium alginate.

In a preferred embodiment, the invention relates to a dry composition comprising from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

(i): from 6 to 9 g of trehalose,
from 0.1 to 1 g of inulin and
from 0.5 to 3 g of hydrolyzed casein, and by
that it does not comprise a salt of alginic acid.

Specifically, the composition does not comprise hydrogen alginate, potassium alginate or sodium alginate.

In a particularly preferred embodiment the dry composition according to the invention comprises 75-80% (w/w) trehalose, 3-10% (w/w) inulin and 15-20% (w/w) hydrolysed casein and does not comprise a salt of alginic acid such as sodium alginate.

The entire disclosure described in the present specification and claims with regard to compositions and methods is evidently included with regard to the above-described preferred embodiment and particularly preferred embodiment. Specifically, the invention relates to an infant powder, a food product or a dietary supplement comprising a composition according to the preferred embodiment and particularly preferred embodiment described above.

The invention further relates to a method for preparing a dry composition according to the invention wherein the method for preparing the dry composition comprises the following steps:

(a): fermenting the LAB cell and harvesting the cells to get a LAB cell concentrate comprising the LAB cells and water—wherein the concentrate comprises from $10^8$ to $10^{11}$ cfu/g dry matter of the concentrate of lactic acid bacteria (LAB) cells;

(b): mixing a suitable amount of protective agent(s) with the LAB cell concentrate to form a slurry—wherein the slurry comprises an amount of protective agent(s) of from 6 to 9 g of trehalose, from 0.1 to 1 g of inulin and from 0.5 to 3 g of hydrolyzed casein and does not comprise a salt of alginic acid—wherein the amount of protective agent(s) is given relative to 1 g of lactic acid bacteria cells in the slurry and both the amount of protective agent(s) and lactic acid bacteria cells are measured as dry matter in a slurry;

(c): freezing the slurry to form solid frozen particles/pellets;

(d): loading a tray with from 2 kg/m² to 50 kg/m² of the frozen particles/pellets to get the herein relevant material on the tray;

(e): primary drying the material on the tray under a vacuum pressure of from 0.7 to 2 millibar(mbar), at a temperature wherein the temperature of the material does not get so high that more than 75% of the LAB cells are inactivated and for a period of time until at least 90% of the water of the slurry of step (b) has been removed; and (f): secondary drying the material of step (e) under a vacuum pressure of from 0.01 to 0.6 millibar(mbar), at a temperature wherein the temperature of the material does not get so high that more than 75% of the LAB cells are inactivated and for a period of time sufficient to reduce the water activity ($a_w$) to less than 0.30 and thereby obtaining the dry composition comprising:

(i): from $10^9$ to $10^{13}$ cfu/g of the composition of lactic acid bacteria cells, wherein the composition is characterized by that it also comprises following amounts of protective agents (all amounts of protective agents below are given relative to 1 g of lactic acid bacteria cells in the composition):

from 6 to 9 g of trehalose,
from 0.1 to 1 g of inulin and
from 0.5 to 3 g of hydrolyzed casein, and by
that it does not comprise a salt of alginic acid.

Compared to a method wherein the composition comprises sodium alginate, mixing step b) is easier as the slurry has a lower viscosity and it is also easier to pelletize in step c) meaning that the particles are often homogeneous and of an appropriate size as explained in further detail below regarding step c) even without a grinding step.

Addition of Other Compounds to the Composition:

The dry composition as described herein may comprise further compounds of interest. This may e.g. be vitamins (e.g. tocopherol) or other compounds one could be interested in having present in the final composition. Examples of such compounds may be moisture scavengers such as e.g. potato starch.

Although the above described drying method is preferred, alternative methods exist as described above. Depending on what method of drying to be used, it may be necessary to add a viscosity modifier. If, for example, vacuum belt drying is intended, it may be necessary to increase the viscosity. Conversely, if spray drying is intended, it may be necessary to decrease the viscosity.

Suitable examples of viscosity modifiers are e.g. water (for decreasing viscosity), pectin, pre-gelatinized starch, gums (e.g. acacia, xanthan, guar gum, locust bean gum), glycerols (e.g. glycerine); glycols (e.g. polyethylene glycols, propylene glycols); plant-derived waxes (e.g. carnauba, rice, candililla), non-plant waxes (beeswax); lecithin; plant fibers; lipids; and silicas (e.g. silicon dioxide).

Use of a Composition According to the Invention:

Generally the specific preferred industrial use of a cell containing composition as described herein would normally depend on the specific characteristics of the cell in question.

The composition may be given to a human, an animal or a fish for health-promoting purposes. This is generally most relevant if the cell has probiotic properties and is particularly relevant when the cell is a probiotic LAB cell.

A preferred formulation of the invention is in the form of an infant powder, whereby the composition is mixed with milk powder. As known in the art—the milk powder may also comprise other supplements.

Another use relates to using the composition as described herein in cereals, such as muesli, or other dry foodstuff.

Accordingly, in further aspects, the invention relates to a food product, such as a cereal, muesli bars, candy bars or chocolate bars, which incorporates the composition according to the invention. It may also be used in powders (e.g. so called sports powders) intended to be mixed in beverages, such as sport drinks or energy drinks.

In another aspect, the invention relates to a dietary supplement comprising a dry composition as described herein.

Below are discussed examples of further herein relevant suitable protective agents. The protective agents used herein are generally those normally used as e.g. cryo-additives in the field, e.g. saccharides, such as trehalose, lactose, maltose, sucrose, raffinose or glucose; myo-inositol; or other so-called cryoprotectants, such as polyethylene glycol, dimethylsulfoxide, glycerol, or dextran. Preferred protective agents are sucrose, and/or maltodextrin.

Other additives, e.g. antioxidants such as ascorbate may also be present. For the purposes of this invention, ascorbate may be termed protective agent.

As discussed herein—an advantage of the herein described novel method for preparing a dry powder composition is that by using the method as described herein one can efficiently dry such LAB compositions having a relatively high amount of carbohydrates (such as e.g. saccharides) as protective agents.

Fermenting the LAB Cell to Get a LAB Cell Concentrate Step (a)

As discussed above—step (a) of the method of the first aspect reads:

"(a): fermenting the LAB cell and harvesting the cells to get a LAB cell concentrate comprising the LAB cells and water—wherein the concentrate comprises from $10^8$ to $10^{14}$ cfu/g dry matter of the concentrate of lactic acid bacteria (LAB) cells"

It is routine work for the skilled person to ferment a LAB cell of interest in order to e.g. produce/grow it in large scale.

As known in the art—harvesting of fermented cells generally involves a centrifugation step to remove relevant parts of the fermentation media and thereby get a LAB cell concentrate.

As known in the art—for herein relevant production of LAB cells one may at this stage have a LAB cell concentrate with around 10% dry matter of cells—i.e. a so-called 10% concentrate. The rest of the concentrate is then normally mainly water—i.e. there will be around 90% of water. The LAB cell concentrate may of course also sometimes contain less water—e.g. around 50% water. Normally—the LAB cell concentrate in step (b) comprises at least 10% (such as at least 20% or at least 50%) of water. In some embodiments, the concentrate may comprise even less than 10% dry matter, such as in the range of 5-10%, e.g. about 5%, In the nrpaent context it is essentially this water of the LAB cell concentrate that is removed by the drying method as described herein to obtain the herein described dry powder LAB composition.

After the harvesting of the cell—it may be preferred to include an extra washing step in order to remove as many of the fermentation media components/compounds as such—i.e. to get a more "pure" LAB cell concentrate that essentially only comprises the LAB cells as such.

The step (a) reads: "wherein the concentrate comprises from $10^8$ to $10^{14}$ cfu/g dry matter of the concentrate of lactic acid bacteria (LAB) cells". The term "dry matter" within the term "cfu/g dry matter" should be understood as the skilled person would understand it in the present context—i.e. that the LAB concentrate comprises the given amount of LAB cells as relative to the dry matter weight of the LAB concentrate (i.e. not including the weight of the liquid as present in the LAB concentrate).

If desired, a step of freezing the LAB concentrate e.g. in the form of solid frozen particles/pellets can be added and the LAB concentrate can be kept as a frozen concentrate for a period of time before being thawed and the process continued with step b). Alternatively, the process can be initiated from step (b) e.g. on the basis of a commercially available LAB cell concentrate.

Mixing Protective Agent(s) with the LAB Cell Concentrate—Step (b):

As discussed above—step (b) of the method of the first aspect reads:

"(b): mixing a suitable amount of protective agent(s) with the LAB cell concentrate to form a slurry—wherein the slurry comprises an amount of protective agent(s) of from 2 g to 40 g—wherein the amount of protective agent(s) is given relative to 1 g of lactic acid bacteria cells in the slurry and both the amount of protective agent(s) and lactic acid bacteria cells are measured as dry matter in a slurry".

The term "slurry" shall be understood as the skilled person would understand it in the present context—i.e. as a relatively thick suspension of solids in a liquid.

It is routine work for the skilled person to mix suitable amount of protective agent(s) with the LAB cell concentrate to get the wanted concentration/amount of protective agent(s) in the slurry.

Freezing the Slurry to Form Solid Frozen Particles/Pellets—Step (c)

As discussed above—step (c) of the method of the first aspect reads:

"(c): freezing the slurry to form solid frozen particles/pellets"

It is routine work for the skilled person to make this freezing the slurry to form solid frozen particles/pellets step as such. As known in the art—it may be done by use of e.g. liquid nitrogen, wherein the slurry is frozen by use of liquid nitrogen to get the solid frozen particles/pellets.

As shown in a working example herein—the present inventors tested different particle sizes of the frozen particles/pellets and it was found that too big particles did not give satisfactory drying results. Accordingly, in a preferred embodiment at least 95% (more preferably at least 97%) of the frozen particles/pellets in step (c) are particles/pellets that are capable of passing through a mesh/sieve with maximum size of the opening/holes of 10 mm.

More preferably, at least 95% (more preferably at least 97%) of the frozen particles/pellets in step (c) are particles/pellets that are capable of passing through a mesh with maximum size of the opening/holes of 7.5 mm, more preferably with maximum size of the opening/holes of 5 mm and most preferably with maximum size of the opening/holes of 3

It is routine work for the skilled person to sieve relevant particles (here the frozen particles/pellets) though a mesh. It is routine work for the skilled person to test if a specific frozen particle/pellet sample is a sample, wherein at least 95% (more preferably at least 97%) of the frozen particles/pellets are particles/pellets that are capable of passing through a mesh with given maximum size of the opening/holes.

As known in the art—one may simply put the specific frozen particle/pellet sample of interest onto a suitable mesh and then move/shake the mesh in a adequate way until no further significant amount of frozen particles/pellets are passing though the mesh—if more than 95% of the frozen particles/pellets have passed through the mesh then is the specific frozen particle/pellet sample of interest a sample, wherein at least 95% of the frozen particles/pellets are particles/pellets that are capable of passing through the mesh with the given maximum size of the opening/holes.

Loading a with Tray Frozen Particles/Pellets—Step (d):

As discussed above—step (d) of the method of the first aspect reads:

"(d): loading a tray with from 2 kg/m² to 50 kg/m² of the frozen particles/pellets to get the herein relevant material on the tray"

In a preferred embodiment—the tray in step (d) of first aspect is loaded with from 5 kg/m² to 30 kg/m² of the frozen particles/pellets (such as e.g. from 7 kg/m² to 15 kg/m² of the frozen particles/pellets).

In the present context one may use any herein suitable tray(s). As known—there are several herein relevant suitable trays available to the skilled person, wherein some of these trays are also commercially available.

As understood by the skilled person in the present context—the tray is normally loaded with frozen particles/pellets in a way wherein one gets relatively even/similar distributions of the frozen particles/pellets in the tray—i.e. one does preferably not have all the frozen particles/pellets situated at e.g. only one edge of the tray.

For e.g. industrial relevant large scale production of relatively big amounts of a herein relevant dry powder composition (e.g. from 100 kg to 10000 kg of the dry powder composition)—it may normally be preferred to simultaneously use more than one (such as e.g. more than 10 or more than 100) trays in e.g. the loading (d) herein—i.e. wherein there in step (d) is loaded more than one (such as e.g. more than 10 or more than 100) trays with from 2 kg/m² to 50 kg/m² of the frozen particles/pellets.

Primary Drying—Step (e):

As discussed above—step (e) of the method of the first aspect reads:

"(e): primary drying the material on the tray under a vacuum pressure of from 0.7 to 2 millibar(mbar), at a temperature wherein the temperature of the material does not get so high that more than 75% of the LAB cells are inactivated and for a period of time until at least 90% of the water of the slurry of step (b) has been removed"

In the present context one may use any herein suitable vacuum drier apparatus. As known—there are several suitable vacuum drier apparatus available to the skilled person, wherein some of these vacuum drier apparatus are also commercially available.

In a preferred embodiment—the vacuum drier apparatus is an apparatus, wherein the heating in the apparatus is so-called radiation heating. As known to the skilled person radiation heating is understood by the skilled person to be different from so-called contact heating. As known to the skilled person—one may get a radiation heating by e.g. having a heating plate situated close to (but not direct contact) with the tray comprising the material to be dried. Said in other words, in relation to primary drying step (e)—there is a space (i.e. vacuum) between the heating plate and the tray—i.e. the heating of the tray is then based on radiation heating.

In a preferred embodiment—the tray is situated between two heating plates, wherein both heating plates provide radiation heating to the tray.

For e.g. industrially relevant large scale production of relatively big amounts of a herein relevant dry powder composition (e.g. from 100 kg to 10000 kg of the dry powder composition)—it may normally be preferred to simultaneously use more than one (such as e.g. more than 10 or more than 100) trays in e.g. drying step (e) herein—i.e. wherein there in step (e) is present more than one (such as e.g. more than 10 or more than 100) trays comprising the material to be dried.

In short, one may see this primary drying (e) as a step, wherein one removes what may be termed "free" water (i.e. contrary to what may be termed "bound" water). In the present context—one may say that this "free" water removed in this step (e) represents the majority of the water present in the LAB cell concentrate of step (a). One may also say that this "free" water is more easy to remove than the "bound" water that one may say is essentially mainly removed in the subsequent secondary drying step (f) of the drying method of the invention (see below for a further discussion of this "bound" water issue).

In this primary drying step the vacuum pressure is from 0.7 to 2 millibar(mbar)—this may be seen as an essential element of this primary drying step (e). As discussed in working examples herein—the present inventors have identified that if one in this primary step (e) uses a vacuum pressure that is different than the range of from 0.7 to 2 millibar(mbar) one does not get a herein satisfactory drying of a LAB composition as described herein (i.e. with a relatively high amount of protective agents).

In short, the present inventors identified that if the vacuum pressure is below 0.7 mbar then may one say that the water in the LAB concentrate is so cold that all the frozen particles/pellets are still completely frozen during a significant part of the time period of this primary drying step (e)—i.e. one may say that this step (e) would then be a virtually 100% so-called freeze-drying step—i.e. where all water is removed by sublimation. The present inventors identified that to remove virtually all water, in this primary drying step, by sublimation does in the present context not give a satisfactory result.

In short, the present inventors identified that if the vacuum pressure is higher than 2 mbar then may one say that the water in the LAB concentrate is so relatively "hot" that a significant part of the frozen particles/pellets get thawed (i.e. are not frozen anymore) during a significant part of the time period of this primary drying step (e)—and the present inventors identified that this is not good in order for that one in the present context gets a satisfactory final drying result.

As known by the skilled person—at 2 mbar pressure the temperature of water (i.e. ice) is −12° C., at 1 mbar the temperature of water (i.e. ice) is −20° C. and at 0.7 mbar pressure the temperature of water (i.e. ice) is −24° C.

In particular at the beginning of this primary drying step (e)—it is normal that the material to be dried has a significant amount of water, since the LAB concentrate of step (a) many times has around e.g. 90% of water and around 10%/a of LAB cells as such.

Accordingly, one may say that in particular at the beginning of this primary drying step (e) it will generally be the temperature of the water that will kind of control the temperature of the material to be dried.

One may say that the present inventors have identified that the vacuum pressure range of from 0.7 to 2 mbar is just the perfect/optimal range for drying the herein relevant LAB compositions (i.e. with a relatively high amount of protective agents).

Without being limited to theory—a reason for that this vacuum pressure range is especially good could be due to that at this pressure the temperature of the water is adequate for that one gets a relatively limited thawing of the frozen particles/pellets of step (c) but there is not a too high thawing of the frozen particles/pellets. Without being limited to theory—one may say that if a limited amount of the frozen particles/pellets are thawed (i.e. get into liquid form)—then it may be that at least some parts of the water is removed by evaporation.

Accordingly, a preferred embodiment herein relates to that a limited (e.g. from at least 0.5% to at maximum 5%, more preferably from at least 1% to at maximum 4%) amount of the material in step (e) is thawed liquid material (i.e. not frozen material). Further, it is preferred that this is so for a significant part (e.g. during at least 3 hours or during at least 6 hours) of the period of time of the primary drying step (e).

The skilled person is visually able to determine if a limited amount of the material in step (e) is thawed liquid material (i.e. not frozen material) by simply observing that there is liquid water present on e.g. the surfaces of the frozen particles/pellets.

As discussed above—in step (e) is read: "at a temperature wherein the temperature of the material does not get so high that more than 75% of the LAB cells are inactivated"

It is routine work for the skilled person to continuously measure the temperature of the material as such during the period of time of step (e). Normally—one simply has one or more thermometer(s) present in the material as such during the period of time of step (e).

As discussed above—one may say that in particular at the beginning of this primary drying step (e) it will generally be the temperature of the water that will kind of control the temperature of the material to be dried.

As discussed above—at the 0.7 to 2 millibar(mbar) pressure used in step (e), the water (i.e. ice) temperature is roughly from −24° C. to −12° C. At this relatively cold temperature (i.e. from roughly from −24° C. to −12° C.) there is generally no herein significant inactivation of the LAB cells.

However, at the end of the period of time of step (e)—there may have been removed e.g. 97% of the so-called "free" water in this step (e)—i.e. there is at this period of time of step (e) significant less water present than at the beginning of the period of time of step (e).

Accordingly, one may say that in particular at the end of the period of time of step (e) it is very important that possible applied heating of the tray/material is well controlled—i.e. so the temperature of the material does not get too high.

In the present context the skilled person will generally know what one may call the heat stability of a herein relevant LAB of interest. Said in other words, it would for a herein relevant LAB of interest be routine work to determine what should be the maximum temperature of the material in order not to get too many of the LAB cells inactivated.

For instance—when the lactic acid bacteria (LAB) cells of point (ii) of the first aspect are *Lactobacillus* cells—it is preferred that the temperature of the material of steps (e) and (f) of the first aspect is a temperature that does not get higher than 40° C.

For instance—when the lactic acid bacteria (LAB) cells of point (ii) of the first aspect are *Bifidobacterium animalis* subsp lactis cells—it is believed that the temperature could be a bit higher without getting a too high inactivation of the cell—i.e. the temperature of the material of steps (e) and (f) of the first aspect is a temperature that does not get higher than e.g. 50° C.

As evident in the present context—there should in step (e) and step (f) preferably be as little inactivation of the LAB cells as possible.

Accordingly, a preferred embodiment relates to step (e), wherein the temperature of the material does not get so high that more than 50% of the LAB cells are inactivated, more preferably the temperature of the material does not get so high that more than 25% of the LAB cells are inactivated, even more preferably the temperature of the material does not get so high that more than 10% of the LAB cells are inactivated and most preferably the temperature of the material does not get so high that more than 2% of the LAB cells are inactivated.

In a preferred embodiment—the primary drying of step (e) of first aspect is done under a vacuum pressure of from 1 to 2 millibar(mbar), such as from 1.1 to 1.7 millibar(mbar).

In a preferred embodiment—in the primary drying of step (e) of first aspect is removed at least 95% of the water of the slurry, more preferably there is removed at least 97% of the water of the slurry and most preferably there is removed at least 98% of the water of the slurry.

A herein preferred embodiment relates to wherein the period of time of step (e) of first aspect is a period from 3 hours to 60 hours—more preferably from 5 hours to 36 hours, even more preferably from 5 hours to 24 hours (such as e.g. from 7 to 15 hours).

Without being limited to theory—it is believed that it for herein industrially relevant large scale production it may be difficult to perform primary drying step (e) properly in less than 3 hours. Without being limited to theory—to use more than 60 hours for drying step (e) would normally not be optimal for a herein industrially relevant large scale production.

Secondary Drying—Step (f):

As discussed above—step (f) of the method of the first aspect reads:

"(f): secondary drying the material of step (e) under a vacuum pressure of from 0.01 to 0.6 millibar(mbar), at a temperature wherein the temperature of the material does not get so high that more than 75% of the LAB cells are inactivated and for a period of time sufficient to reduce the water activity ($a_w$) to less than 0.30 and thereby obtaining the dry powder composition comprising:

(i): from $10^8$ to $10^{14}$ cfu/g of the composition of lactic acid bacteria (LAB) cells; and (ii) an amount of protective agent(s) of from 2 g to 40 g—wherein the amount of protective agent(s) is given relative to 1 g of lactic acid bacteria cells in the dry composition."

As understood by the skilled person—a number of the technical issues discussed for primary drying step (e) above may also be of corresponding relevance with respect to the secondary drying step (f). For instance—the vacuum drying apparatus used in step (f) is many times the same (or very similar) vacuum drying apparatus as used in the step (e).

In short, one may see this secondary drying (f) as a step, wherein one removes what may be termed "bound" water (i.e. contrary to what may be termed "free" water as generally removed in step (e)—see discussion above). As known to the skilled person—one may say that the "bound" water is more difficult to remove than the "free" water—accordingly, there is used more vacuum (less mbar pressure) in step (f) as compared to step (e).

A herein preferred embodiment relates to wherein the secondary drying of step (f) of first aspect is done under a vacuum pressure of from 0.05 to 0.4 millibar(mbar), such as from 0.1 to 0.3 millibar(mbar).

In the present context—a pressure of around 0.2 mbar may sometimes be termed "full vacuum".

As discussed above—there should in step (e) and step (f) preferably be as little inactivation of the LAB cells as possible.

Accordingly, a preferred embodiment relates to step (f), wherein the temperature of the material does not get so high that more than 50% of the LAB cells are inactivated, more preferably the temperature of the material does not get so high that more than 25% of the LAB cells are inactivated, even more preferably the temperature of the material does not get so high that more than 10% of the LAB cells are inactivated and most preferably the temperature of the material does not get so high that more than 2% of the LAB cells are inactivated.

As discussed in relation to step (e) above—when the lactic acid bacteria (LAB) cells of point (ii) of the first aspect are *Lactobacillus* cells—it is preferred that the temperature of the material of steps (e) and (f) of the first aspect is a temperature that does not get higher than 40° C.

For instance—when the lactic acid bacteria (LAB) cells of point (ii) of the first aspect are *Bifidobacterium animalis* subsp lactis cells—it is believed that the temperature could be a bit higher without getting a too high inactivation of the cells—i.e. the temperature of the material of steps (e) and (f) of the first aspect is a temperature that does not get higher than e.g. 50° C.

As discussed above, at the end of the period of time of primary drying step (e)—there may have been removed e.g. 97% of the so-called "free" water in this step (e)—i.e. there is at the end of step (e) significant less water present than at the beginning of the period of time of step (e).

In line of this—it is evident that there during the secondary drying step (f) is relatively little water present.

Accordingly, if any heating is applied in this secondary drying step (f)—the e.g. used heating plates (for e.g. radiation heating—see above) will generally be set to a heating temperature that is very close the temperature one wants to have as the temperature of the material (to be dried) as such. For instance—if the temperature of the material (to be dried) as such in step (f) shall at maximum be e.g. 37° C.—then will e.g. used heating plates not be set to a temperature significantly above this 37° C.

A herein preferred embodiment relates to wherein the period of time of step (f) of first aspect is a period from 3 hours to 60 hours—more preferably from 5 hours to 36 hours, even more preferably from 5 hours to 24 hours (such as e.g. from 7 to 15 hours).

Without being limited to theory—it is believed that it for herein industrial relevant large scale production it may be difficult to perform primary drying step (f) properly in less than 3 hours. Without being limited to theory—to use more than 60 hours for drying step (f) would normally not be optimal for a herein industrially relevant large scale production.

In a preferred embodiment—the period of time of step (f) is a period of time sufficient to reduce the water activity ($a_w$) to less than 0.25, more preferably less than 0.20 and most preferably to less than 0.15.

The skilled person knows how to determine the water activity ($a_w$) of dry composition as described herein.

Other Optional Steps:

As understood by the skilled person—the drying method of the first aspect as discussed herein may comprise further optional steps.

A herein obvious relevant optional extra step would be to e.g. properly packaging the in step (f) obtained dry powder composition.

As known in the art—the package may e.g. be a bottle, box, vial, capsule etc—preferably the package is waterproof to maintain the water activity of the dry powder composition low.

Further herein obvious relevant optional extra steps include use of the in step (f) obtained dry powder LAB composition for a herein commercial relevant use.

Just as an example—commercially relevant uses could e.g. be as an infant powder, whereby the dry powder LAB composition is mixed with milk powder—or use to make a dairy product.

EXAMPLES

Materials and Methods

Washed concentrate of *Lactobacillus rhamnosus* LGG@ and *Lactobacillus paracasei* subsp. *paracasei* L. *casei* 431@—obtainable from Chr. Hansen A/S, Denmark Trehalose from Cargill name: Treha 16400

Enzymatically Hydrolyzed Casein from DMV International

Na-alginate from FMC BioPolymer: Manugel@ DMB

Inulin from BENEO-ORAFTI: Orafti® DMB

Maltodextrin: Glucidex IT 12 from Roquette

Na-ascorbate from Northeast Pharmaceutical group Co.,

Sucrose from Nordic Sugar: Granulated sugar 550

Remy HC-P (pregelatinised rice) starch, baby food grade from Beneo-remy NV Infant powder was EnfaGrow sourced from Mead Johnson LCC, Evansville, Ind.

Example 1

Drying of LAB Composition

The Lactic acid bacteria (LAB) cell was the commercially available *Lactobacillus* cell LGG®—obtainable from Chr. Hansen A/S, Denmark.

The vacuum drier apparatus was an apparatus, wherein the heating in the apparatus was so-called radiation heating. The tray was situated between two heating plates, wherein both 10 heating plates provide radiation heating to the tray.

Step (a):

1 kg of LAB cell concentrate was obtained—it comprises around 10% dry matter of cells—i.e. a so-called 10% concentrate with around 90% of water.

Step (b):

1 kg of a mixture of protective agents (the mixture comprised 30 g Sodium Alginate; 50 g Inulin, 753 g Trehalose and 167 g Casein Hydrolysate) was mixed with the LAB cell concentrate.

Accordingly was obtained a slurry that comprised an amount of protective agents of around 10 g—wherein the amount of protective agents is given relative to 1 g of lactic acid bacteria cells in the slurry and both the amount of protective agent(s) and lactic acid bacteria cells are measured as dry matter in a slurry.

Step (c):

The slurry was frozen to form solid frozen particles/pellets. It was done by use of liquid nitrogen.

Step (d):

Trays were loaded with 10 kg/m² of the frozen particles/pellets to get the herein relevant material on the trays.

Step (e):

Primary drying of the material on the tray was performed under different vacuum pressures—some were within the vacuum pressure range of from 0.7 to 2 millibar(mbar) (e.g. was used 1.3 mbar pressure) and some were performed outside this range (e.g. was used 2.5 mbar pressure).

This step was performed at a temperature wherein the temperature of the material did not get higher than 37° C.

At this maximum temperature significantly less than 50% of the LAB cells were inactivated.

This step was performed a period of time until at least 97% of the water of the slurry of step (b) had been removed—this took around 12 hours.

Step (f):

Secondary drying the material of step (e) was performed under a vacuum pressure of 0.2 mbar.

As for step (e)—this step was also performed at a temperature wherein the temperature of the material did not get higher than 37° C. This step was performed a period of time of around 12 hours.

Results:

TABLE 1

Water activity and process survival at two different pressures

|  | # 1 | # 2 | # 3 | # 4 |
|---|---|---|---|---|
| Tray load | 10 kg/m2 | 8 kg/m2 | 10 kg/m2 | 8 kg/m2 |
| Heating temp. | 50° C. | 50° C. | 50° C. | 50° C. |
| Max product temp | 32° C. | 32° C. | 40° C. | 32° C. |
| Pressure | 2.5/0.2 mbar | 2.5/0.2 mbar | 2.5/0.2 mbar | 1.3/0.2 mbar |
| Drying time | 23 hours | 23 hours | 23 hours | 23 hours |
| Aw | 0.29 | 0.25 | 0.25 | 013 |
| % active cells | 34 | 26 | 34 | 40 |

From table 1 it is seen that within the products dried at 2.5 mbar the water activity is higher than preferred (<0.15) whereas the sample dried at 1.3 mbar has a water activity as preferred. The process survival is furthermore higher for the sample at 1.3 mbar than for the samples dried at 2.5 mbar.

TABLE 2

Water activity and process survival at different temperatures

|  | # 5 | # 6 | # 7 |
|---|---|---|---|
| Tray load | 10 kg/m2 | 10 kg/m2 | 10 kg/m2 |
| Heating temp. | 60° C. | 70° C. | 60° C. |
| Niax product temp. | 32° C. | 32° C. | 37° C. |
| Pressure | 1.3/0.2 mbar | 1.3/0.2 mbar | 1.3/0.2 mbar |
| Drying time | 31 hours | 24 hours | 24 hours |
| Aw | 0.11 | 0.33 | 0.12 |
| % active cells | 63 | 26 | 65 |

From table 2 it is seen that the water activity as well as the process survival is in an unacceptable range when the drying temperature is too high (70° C.) whereas there is no differences on neither the water activity nor process survival whether the drying temperature is 50 or 60° C. In both cases the values are in an acceptable range.

For this example—one may say that the herein essential parameter that was varied was in primary drying step (e)—wherein different vacuum pressures were used—some were within the vacuum pressure range of from 0.7 to 2 millibar (mbar) (e.g. was used 1.3 mbar pressure) and some were performed outside this range (e.g. was used 2.5 mbar pressure).

The experimental results essentially demonstrated that when there was used a vacuum pressure outside the range of 0.7 to 2 mbar there was not obtained a herein satisfactory drying of the LAB composition. The pressure is to be selected to be slightly above the transition temperature of the formulation for the reasons previously explained. The transition temperature of the formulation used in example 1 is about −33° C. At 2.5 mbar the temperature is about −10.5° C. which is much higher than the transition temperature. The results in table 1 thus demonstrate that 1.3 mbar is more suitable.

When the vacuum pressure was within the range of from 0.7 to 2 millibar(mbar) (e.g. 1.3 mbar pressure) then it was possible to make a proper and efficient drying to get the dry formula composition with a water activity ($a_w$) of less than 0.15.

Conclusions:

The results of this Example 1 essentially demonstrated that it is only by working within the vacuum pressure range of from 0.7 to 2 mbar in step (e) that one gets a herein satisfactory method for drying a herein relevant LAB composition comprising relatively high amount of protective agents.

Example 2

Particle Size of Frozen Particles/Pellets of Step (c)

An experiment was made essentially as described for Example 1—but wherein the vacuum pressure in step (c) was kept constant at around 1.3 mbar pressure.

In this experiment the essential variable was the particle size of frozen particles/pellets of step (c).

Experiments were made, wherein at least 97% of the frozen particles/pellets in step (c) were particles/pellets that were capable of passing through a mesh with maximum size of the opening/holes of different sizes.

Results:

The experimental results essentially demonstrated that when the sizes of the particles/pellets were above 10 mm then there was not obtained an optimal drying result.

But when the sizes of the particles/pellets were below 5 mm then there was obtained very good and efficient drying, Conclusions:

The results of this Example 2 essentially demonstrated that it is herein preferred that at least 95% (more preferably at least 97%) of the frozen particles/pellets in step (c) are particles/pellets that are capable of passing through a mesh with maximum size of the opening/holes of 10 mm (preferably with maximum size of the opening/holes of 5 mm).

Example 3

Drying of Other LAB Compositions

Example 1 was essentially repeated but with use of other LAB cells and other protective agents. Drying at pressures of 0.9/0.2 mbar and heating temperatures of 32° C. and 37° C. has been evaluated as well (for formulations with and without alginate) and for both temperatures the water activity of the dry products were <0.15 after 24 hours of drying.

The formulations without alginate and the formulations with sucrose were run as #7 and resulted in dry products with water activity <0.15 and process survival of ~50%. The sucrose formulation resulted in dry products with water activity <0.3 but by increasing the drying time the water activity might be much lower.

For step (b) were in all experiments obtained a slurry that comprised an amount of protective agents of around 6 g to 15 g—wherein the amount of protective agents is given relative to 1 g of lactic acid bacteria cells in the slurry and both the amount of protective agent(s) and lactic acid bacteria cells are measured as dry matter in a slurry.

For all the experiments—at least 50% of the used protective agents were saccharides.

Conclusions:

The results of this Example 3 essentially demonstrated the same as in Example 1—i.e. that it is only by working within the vacuum pressure range of from 0.7 to 2 mbar in step (e) that one gets a herein satisfactory method for drying a herein relevant LAB composition comprising relatively high amount of protective agents. The exact vacuum pressure range suitable for the individual composition is selected by determining the transition temperature of the composition and correlating it with a water vapour pressure table as explained above.

One may say that this Example 3 confirmed this conclusion for different LAB compositions that may be characterized as comprising a relatively high amount of saccharides as protective agents.

Example 4

Preparation of Formulations without Alginate

To one part LGG® concentrate was added two parts demineralized water and the concentrate was centrifuged back to the original volume ($-1.27 \times 10^{11}$ active cells/g). The cell concentrate used below had around 10% dry matter of cells—i.e. a so-called 10% concentrate.

Formulation 1: To 100 g washed concentrate was added 30 g sucrose+17.5 g maltodextrin (Glucidex IT 12)+13 g Na-ascorbate. The mixture was stirred until the additives were dissolved. Afterwards the mixture was vacuum dried.

Formulation 2: To 100 a washed concentrate was added 70 n cIrrrnse+17.5 g maltodextrin (Glucidex IT 12)+13 g Na-ascorbate. The mixture was stirred until the additives were dissolved. Afterwards the mixture was vacuum dried.

Formulation 3: To 100 g washed concentrate was added 37.4 g sucrose+60 g Trehalose+2.6 g Na-ascorbate. The mixture was stirred until the additives were dissolved. Afterwards the mixture was vacuum dried.

Reference 1 (reference formulation): To 100 g washed concentrate was added 6 g sucrose+3.5 g maltodextrin (Glucidex IT 12)+2.6 g Na-ascorbate. The mixture was stirred until the additives were dissolved. Afterwards the mixture was vacuum dried.

If the mixtures are dried in a vacuum belt dryer it might be necessary to add a small amount of gelatinizing agent e.g. pectin to get an appropriate viscosity Example 5

Test of LGG® Formulations without Alginate in Open Bags and in Infant Powder at 30° C.

The stability of the products has been tested in open bags stored at 30° C. and 30% RH and when mixed into infant powder with a water activity of 0.3. See stability data in Table 3 and Table 4. As reference is used a LGGC) containing 20% of the amount of additives in Formulation 1 as outlined in Example 4 above. The powder was moisturized to obtain a water activity of 0.27-0.30.

TABLE 3

Storage in open bags stored at 30° C./30% RH.

| Formulation | Start Log active cells/g | 1 week Log active cells/g | 10 days Log active cells/g | 2 weeks Log active cells/g | 3 weeks Log active cells/g | Log loss 3 weeks |
|---|---|---|---|---|---|---|
| Formulation 1 | 11.3 | 11.3 | 11.3 | 11.3 | 11.3 | 0 |
| Formulation 2 | 11.0 | 11.0 | 11.0 | 11.0 | 11.0 | 0 |
| Formulation 3 | 11.0 | 11.0 | 11.1 | 11.1 | 11.0 | 0 |
| Reference 1 | 11.5 | 11.4 | — | 11.2 | 11.0 | 0.5 |

The samples a e measured by Flow Cytometry (active cells/g).

Conclusion:

From Table 3 it is seen that the highest loss of % active cells is found in Reference 1. By increased (comparison of Formulation 1 and Reference 1). Also formulations 2 and 3 demonstrate an increased stability.

TABLE 4

Storage stability at 30° C. in Enfagrow with $a_w$: 0.3.

| Formulation | Start Log CFU/g | 9 weeks Log CFU/g | 15 weeks Log CFU/g | Log loss 9 weeks | Log loss 15 weeks |
|---|---|---|---|---|---|
| Formulation 1 | 11.4 | 10.9 | 11.1 | 0.5 | 0.3 |
| Formulation 2 | 11.1 | 11.0 | 10.9 | 0.1 | 0.2 |
| Formulation 3 | 11.2 | 10.8 | 10.7 | 0.4 | 0.5 |
| Reference 1 | 11.5 | 8.0 | 5.7 | 3.5 | 5.8 |

The bags were flushed with N2 and sealed before storage.

Conclusion:

The infant powders made with formulations 1-3 have a better stability than Reference 1.

Example 6

Test of *L. paracasei* Subsp. *paracasei L. casei* 431® Formulations without Alginate in Infant Powder at 35° C.

To one part *L. paracasei* subsp. *paracasei L. casei* 431® concentrate (LC 431) was added two parts demineralized water and the concentrate was centrifuged back to the original volume ($-1.27 \times 10^{11}$ active cells/g). The cell concentrate used below had around 10% dry matter of cells—i.e. a so-called 10% concentrate.

Formulation $1_{LC\ 431}$: To 100 g washed concentrate was added 30 g sucrose+17.5 g maltodextrin (Glucidex IT 12)+13 g Na-ascorbate. The mixture was stirred until the additives were dissolved. Afterwards the mixture was pelletised in liquid nitrogen before it was vacuum dried.

The mixture was added to infant powder and the stability of the product tested in an infant powder with a water activity of 0.3 stored at 30% RH at 35° C. See stability data in Table 3. As reference is used infant powder containing LC 431 in Reference 1 as outlined in Example 4 above.

TABLE 5

Storage stability at 35° C. in infant powder with $a_w$: 0.3.

| Formulation | Start Log CFU/g | 3 weeks Log CFU/g | 6 weeks Log CFU/g | 9 weeks Log CFU/9 | Log loss |
|---|---|---|---|---|---|
| Formulation $1_{LC\,431}$ | 10.0 | 9.3 | 9.4 | 9.1 | 0.9 |
| Reference $1_{LC\,431}$ | 11.9 | 9.9 | 9.1 | 7.7 | 4.2 |

The bags were flushed with N2 and sealed before storage.

Conclusion:

From Table 5 and FIG. 1 it is seen that also for *L. casei* 431® and at a storage temperature of 35° C. the highest loss of % active cells is found in Reference 1. By increasing the amount of protective agents by a factor 5 the stability is significantly increased also for *L. casei* 431®.

Example 7

Test of Six Different *L. paracasei* Subsp. *paracasei L. casei* 431® Formulations without Alginate in Infant Powder at 35° C.

To one part *L. casei* 431® concentrate was added two parts demineralized water and the concentrate centrifuged back to the original volume (~1.27×10$^{11}$ active cells/g). The cell concentrate used below had around 10% dry matter of cells—i.e. a so-called 10% concentrate. The mixture was stirred until the additives were dissolved. Afterwards the mixture was pelletised in liquid nitrogen before it was vacuum dried.

Composition 1: To 1000 g washed concentrate was added 753 g trehalose+191 g maltodextrin+26 g Na-ascorbate+30 g Remy HC-P, Composition 2: To 1000 g washed concentrate was added 753 g trehalose+50 g inulin+167 g hydrolysed casein.

Composition 3: To 1000 g washed concentrate was added 366 g trehalose+213 g maltodextrin+26 g Na-ascorbate.

Composition 6: To 1000 g washed concentrate was added 615 g trehalose+358 g maltodextrin+26 g Na-ascorbate.

Composition 7: To 1000 g washed concentrate was added 459 g trehalose+267 g maltodextrin+26 g Na-ascorbate.

Composition 8: To 1000 g washed concentrate was added 213 g trehalose+124 g maltodextrin+26 g Na-ascorbate.

The various compositions were added to infant powder and the stability of the products tested in infant powder with a water activity of 0.3 stored at 30% RH at 35° C. in sealed bags flushed with $_{N2}$. See stability data in Table 4 and FIG. 2. As reference is used infant powder containing *L. casei* 431® in Reference 1 described in Example 4 above.

TABLE 6

Storage stability (log active cells/g) at 35° C. in infant powder with $a_w$: 0.3.

| Composition | 0 | 3 weeks | 5 weeks | 6 weeks | 9 weeks | 13 weeks | 17 weeks |
|---|---|---|---|---|---|---|---|
|  | 10.5 | 9.4 | — | 9.7 | 8.7 | 8.4 | — |
| 2 | 10.7 | 10.4 | — | 10 | 9.5 | 9.6 | 9.4 |
|  | 10.8 | 9.4 | — | 9 | 8.8 | 8.6 | — |
| 6 | 10.4 | 93 | — | 8.8 | 8.8 | 8 | — |
| 7 | 10.3 | 9.3 | — | 8.6 | 8.6 | 8 | — |
| 8 | 10.7 | 9.6 | — | 8.9 | — | 8.5 | — |
| Reference 1 | 12.0 | 9.0 | 7.8 | — | — | — | — |

Figure 2:
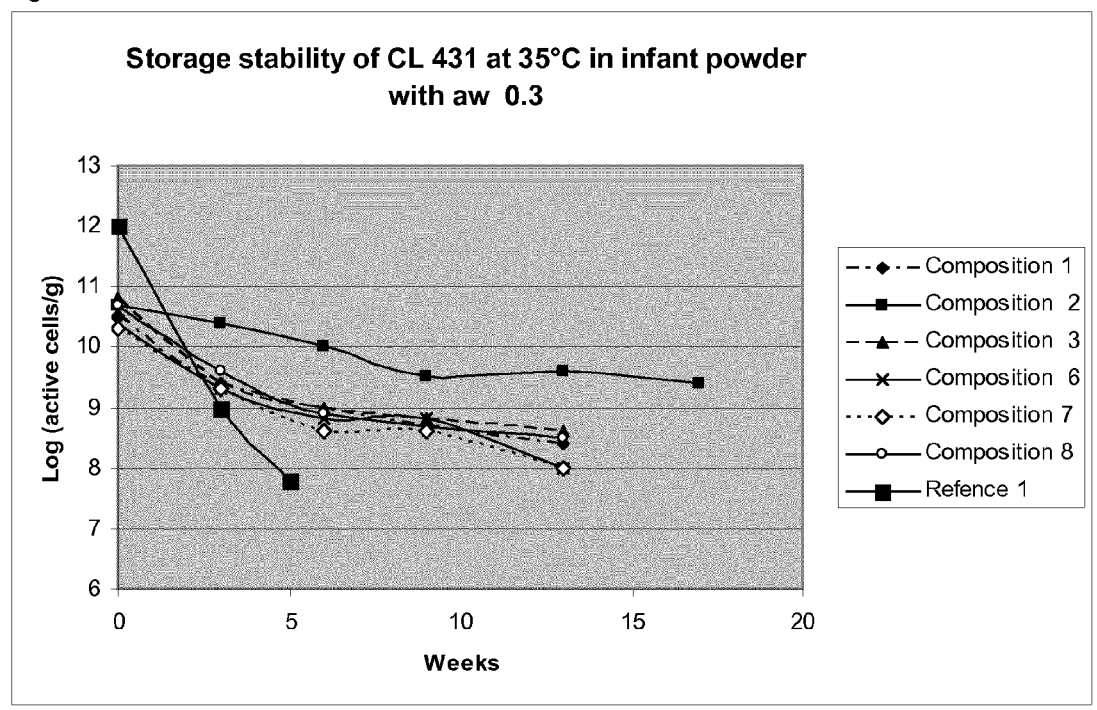
FIG. 2 shows storage stability for six different *L. casei* 431® compositions in infant powder with $a_w$: 0.3 and at a storage temperature of 35° C.
Figure 3:
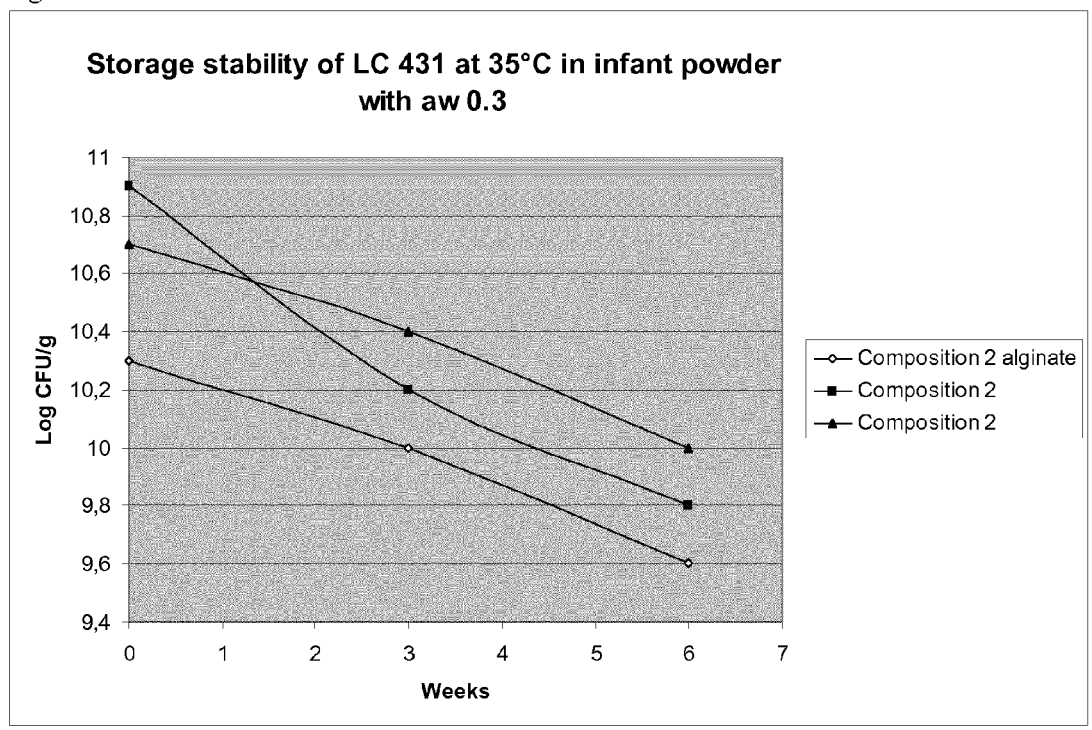
FIG. 3 shows storage stability for *L. casei* 431® compositions in infant powder with $a_w$: 0.3 and at a storage temperature of 35° C.
Figure 4:
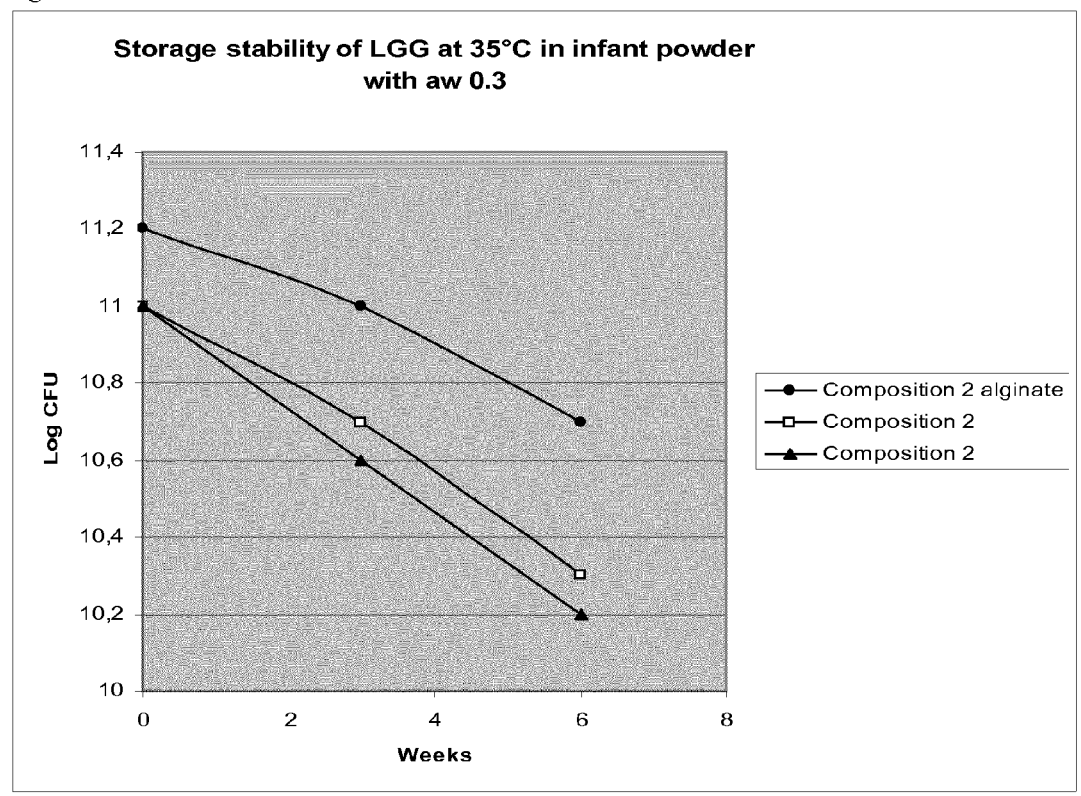
FIG. 4 shows storage stability for LGG@ compositions in infant powder with $a_w$: 0.3 and at a storage temperature of 35° C.
Figure 5:
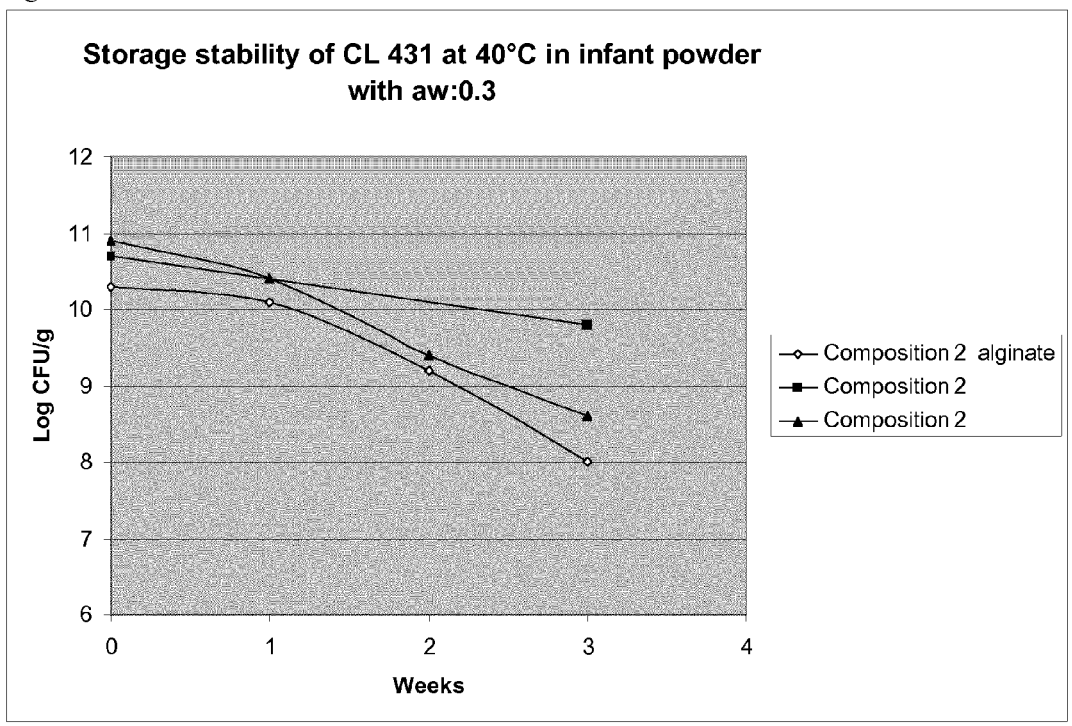
FIG. 5 shows storage stability for *L. casei* 431C) compositions in infant powder with $a_w$: 0.3 and at a storage temperature of 40° C.
Figure 6:
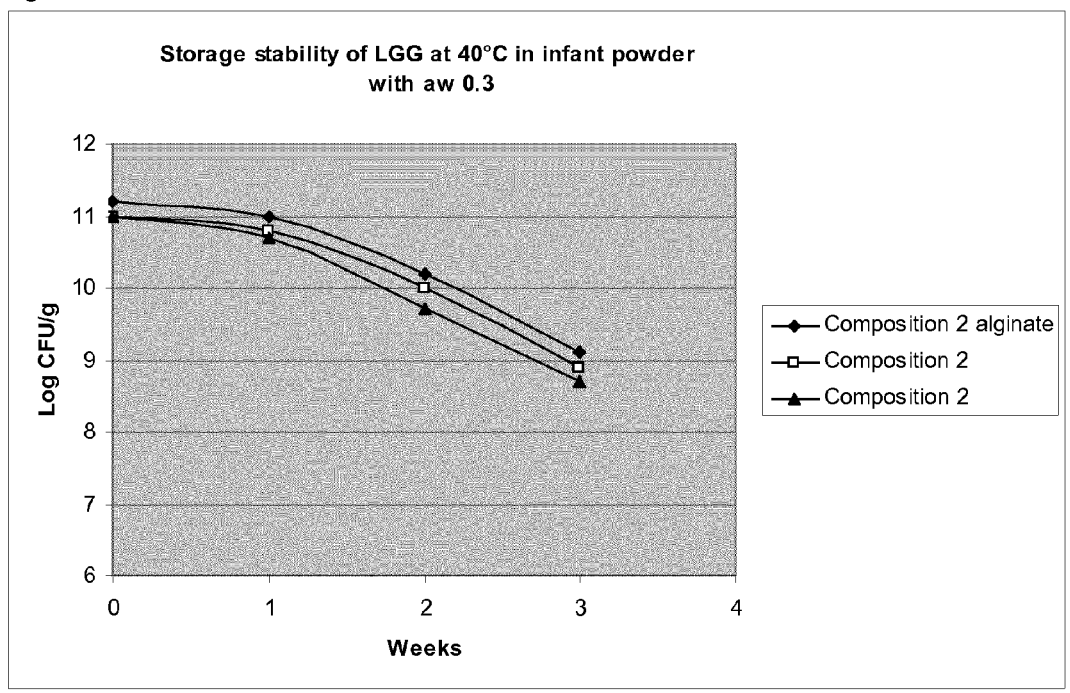
FIG. 6 shows storage stability for LGG® compositions in infant powder with $a_w$: 0.3 and at a storage temperature of 40° C.

Conclusion:

From Table 6 and FIG. 2 it is seen that for *L. casei* 431® and at a storage temperature of 35° C. the highest loss of °/0 active cells is found in Reference 1. All the tested compositions and in particular composition 2 demonstrate a substantially improved stability.

Example 8

Comparison of Compositions with and without Alginate for *L. Paracasei* Subsp. *paracasei* (LC 431) and for LGGC)

10% concentrates of LGG and *L. paracasei* subsp. paracasei (LC 431) were prepared as described above and added to composition 2 or to composition $2_{alginate}$ (see below). Two different LGG® concentrates and two different *L. casei* 431® concentrates were used in order to test reproducibility. Further, two different formulations were prepared, the difference between the two formulations being that composition 2 does not contain alginate whereas composition $2_{alginate}$ contains 30 g Na-alginate per kg washed concentrate. The mixture was stirred until the additives were dissolved and frozen in liquid nitrogen. Afterwards the mixture was vacuum dried.

Composition $2_{alginate}$: To 1000 g washed concentrate was added 753 g trehalose+50 g inulin+167 g hydrolysed casein+30 g Na-alginate.

TABLE 7a

Storage stability data (log (CFU/g) after storage at 35° C. in infant powder with $a_w$: 0.3 in sealed bags

| | 0 weeks | 1 Week | 2 Weeks | 3 Weeks | 5 Weeks | 6 Weeks |
|---|---|---|---|---|---|---|
| Composition $2_{LGG+Na-alginate}$ | 11.2 | — | — | 11 | — | 10.7 |
| Composition $2_{LGG}$ | 11.0 | — | — | 10.7 | — | 10.3 |
| Composition $2_{LGG}$ | 11.0 | — | — | 10.6 | — | 10.2 |
| Composition $2_{LC\,431+Na-alginate}$ | 10.3 | — | — | 10 | — | 9.6 |
| Composition $2_{LC\,431}$ | 10.9 | — | — | 10.2 | — | 9.8 |
| Composition $2_{LC\,431}$ | 10.7 | — | — | 10.4 | — | 10.0 |

TABLE 7b

Storage stability data (log (CFU/g) after storage at 40° C. in infant powder with $a_w$: 0.3 in sealed bags.

| | 0 Weeks | 1 Week | 2 Weeks | 3 Weeks |
|---|---|---|---|---|
| Composition $2_{LGG+Na-alginate}$ | 11.2 | 11 | 10.2 | 9.1 |
| Composition $2_{LGG}$ | 11.0 | 10.8 | 10.0 | 8.9 |
| Composition $2_{LGG}$ | 11.0 | 10.7 | 9.7 | 8.7 |
| Composition $2_{LC\,431+Na-alginate}$ | 10.3 | 10.1 | 9.2 | 8.0 |
| Composition $2_{LC\,431}$ | 10.7 | — | — | 9.8 |
| Composition $2_{LC\,431}$ | 10.9 | 10.4 | 9.4 | 8.6 |

Conclusion:

From Tables 7a and 7b and FIGS. 3-6 it is demonstrated that there is substantially no difference between compositions with or without Na-alginate with regard to stability.

Example 9

Heat Treatment of Compositions of LGG® with and without Alginate

10% concentrates of LGGC) were prepared and added to composition 2 or to composition $2_{aliginate}$ as described in Example 8 above. As heat treatment is relevant for production scale products two of the compositions were subjected to heat treatment in order to compare the stability of the compositions with or without alginate. As reference is used infant powder containing LGGC) in Reference 1 described in Example 4 above.

TABLE 8

Storage stability data (log (CFU/g) after storage at 35° C. in infant powder with $a_w$: 0.25 in sealed bags

| | 0 weeks | 3 Week | 6 Weeks | 9 Weeks | 13 Weeks | 17 Weeks |
|---|---|---|---|---|---|---|
| Composition 2$_{alginate}$ | 11.1 | 11 | 10.9 | 10.9 | 10.7 | 10.6 |
| Composition 2- | 10.9 | 10.8 | 10.7 | 10.6 | 10.5 | 10.5 |
| Composition 2$_{alginate+heat}$ | 11.0 | 10.9 | 10.8 | 10.5 | 10.3 | 10.2 |
| Composition 2$_{heat}$ | 10.8 | 10.8 | 10.6 | 10.5 | — | 10.4 |
| Reference 1 | 11.9 | 11.5 | 11.2 | 110 | 10.7 | 9.8 |

Figure 7:
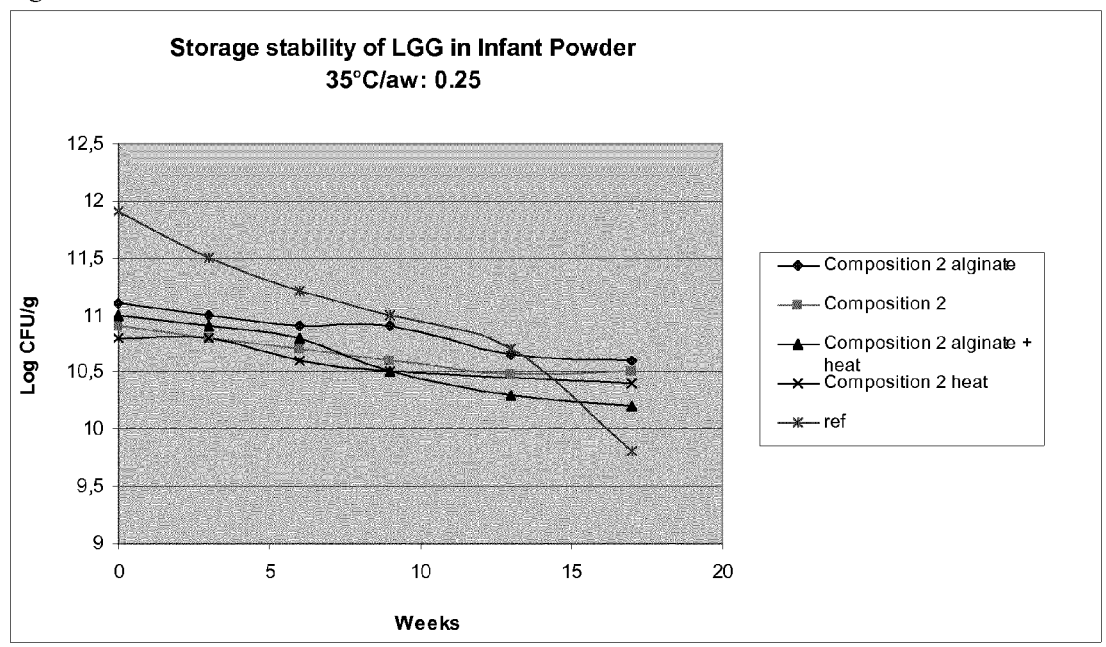
FIG. 7 shows storage stability for LGG@ compositions in infant powder with $a_w$: 0.25 and at a storage temperature of 35° C.

Conclusion:

From Table 8 and FIG. 7 it is seen that for the composition with sodium alginate the heat treatment has a negative impact on stability.

The invention claimed is:

1. A stable dry composition of lactic acid bacteria cells comprising:
   (a) from $10^9$ to $10^{13}$ cfu lactic acid bacteria cells per gram of the composition; and
   (b) protective agents in amounts effective to stabilize the lactic acid bacteria in the composition comprising
       (i) from 2 to 9 g of sucrose per gram of the lactic acid bacteria cells;
       (ii) from 1 to 3 g of maltodextrin per gram of the lactic acid bacteria cells; and
       (iii) from 0.75 to 2 g of Na-ascorbate per gram of the lactic acid bacteria cells.

2. The dry composition according to claim 1, wherein the lactic acid bacteria is at least one selected from the group consisting of: *Lactococcus* species, *Streptococcus* species, *Enterococcus* species, *Lactobacillus* species, *Leuconostoc* species, *Bifidobacterium* species, *Propioni* and *Pediococcus* species.

3. The dry composition according to claim 1, wherein the lactic acid bacteria is at least one selected from the group consisting of: *Lactobacillus rhamnosus*, *Lactococcus lactis* subsp. *lactis*, *Lactococcus lactis* subsp. *cremoris*, *Leuconostoc lactis*, *Leuconostoc mesenteroides* subsp. *cremoris*, *Pediococcus pentosaceus*, *Lactococcus lactis* subsp. *lactis* biovar. *diacetylactis*, *Lactobacillus casei* subsp. *casei*, *Streptococcus thermophilus*, *Enterococcus faecum*, *Bifidobacterium animalis*, *Bifidobacterium lactis*, *Bifidobacterium longum*, *Lactobacillus lactis*, *Lactobacillus helveticus*, *Lactobacillus fermentum*, *Lactobacillus salivarius*, *Lactobacillus delbrueckii* subsp. *bulgaricus* and *Lactobacillus acidophilus*.

4. The dry composition according to claim 1, wherein the weight of the dry composition is from 50 g to 10000 kg.

5. An infant powder comprising a composition according to claim 1.

6. An infant formula, follow-on formula, growing up milk or special formula or infant and children's nutritional product comprising the infant powder of claim 5.

7. A food product comprising a composition according to claim 1.

8. A dietary supplement comprising a composition according to claim 1.

9. The dry composition according to claim 1, wherein the lactic acid bacterium is at least one selected from the group consisting of *Bifidobacterium animalis* subsp *lactis* deposited as DSM 15954, *Bifidobacterium animalis* subsp *lactis* deposited as ATCC 27536, *Biliclobacterium animalis* subsp *lactis* deposited as DSM 10140, *Lactobacillus acidophilus* deposited as DSM 13241, *Lactobacillus rhamnosus* deposited as ATCC 53103, *Lactobacillus rhamnosus* deposited as ATCC 55826, *Lactobacillus reuteri* deposited as ATCC 55845, *Lactobacillus paracasei* subsp. *paracasei* deposited as ATCC 55544, *Lactobacillus paracasei* deposited as LMG-17806, *Streptococcus thermophilus* deposited as DSM 15957, *Lactobacillus fermentum* deposited as NM02/31074, and *Lactobacillus paracasei* subsp. *paracasei* deposited as CCTCC M204012.

10. The dry composition according to claim 1, wherein the lactic acid bacteria in the composition are stable when stored at 30° C. and 30% relative humidity.

11. The dry composition according to claim 1, wherein the lactic acid bacteria in the composition exhibit increased stability when stored at 30° C. and 30% relative humidity as compared to a comparable composition lacking the effective amounts of the protective agents.

12. The dry composition according to claim 1, wherein the water activity ($a_w$) of the dry composition is less than 0.30.

13. The dry composition according to claim 1, made by a process comprising mixing an aqueous preparation of the lactic acid bacteria cells with the sucrose, maltodextrin, and Na-ascorbate to form a mixture, and drying the mixture.

14. The dry composition according to claim 13, wherein the mixture is dried under a vacuum pressure of 0.7 to 2 mbar.

* * * * *